(12) United States Patent
Lee et al.

(10) Patent No.: US 12,303,354 B2
(45) Date of Patent: May 20, 2025

(54) ALIGNMENT STATE INDICATING APPARATUS AND METHOD

(71) Applicant: MEDIT CORP., Seoul (KR)

(72) Inventors: Dong Hoon Lee, Seoul (KR); Soo Bok Lee, Seoul (KR)

(73) Assignee: MEDIT CORP., Seoul (KR)

( * ) Notice: Subject to any disclaimer, the term of this patent is extended or adjusted under 35 U.S.C. 154(b) by 275 days.

(21) Appl. No.: 17/897,126

(22) Filed: Aug. 27, 2022

(65) Prior Publication Data

US 2022/0409347 A1 Dec. 29, 2022

Related U.S. Application Data

(63) Continuation of application No. PCT/KR2021/002446, filed on Feb. 26, 2021.

(30) Foreign Application Priority Data

Feb. 28, 2020 (KR) .................. 10-2020-0025433
Feb. 25, 2021 (KR) .................. 10-2021-0025633

(51) Int. Cl.
*A61C 9/00* (2006.01)
*G06F 3/01* (2006.01)

(52) U.S. Cl.
CPC ............ *A61C 9/0053* (2013.01); *G06F 3/016* (2013.01)

(58) Field of Classification Search
CPC .............................. A61C 9/0053; G06F 3/016
See application file for complete search history.

(56) References Cited

U.S. PATENT DOCUMENTS 5,725,376 A * 3/1998 Poirier ................. A61C 9/0053
433/172
5,967,777 A * 10/1999 Klein ................... A61C 9/0053
433/76

(Continued)

FOREIGN PATENT DOCUMENTS

KR 10-2016-0014470 A 2/2016
KR 10-2016-0020268 A 2/2016

(Continued)

OTHER PUBLICATIONS

International Search Report mailed Jul. 29, 2021 for International Application No. PCT/KR2021/002446 and its English translation.

(Continued)

*Primary Examiner* — Nicholas D Lucchesi
(74) *Attorney, Agent, or Firm* — Insight Law Group, PLLC; Seung Lee

(57) ABSTRACT

The present invention provides an alignment state indicating apparatus and an alignment state indicating method implemented by the apparatus, the apparatus comprising: a case having an opening which is open so that an object in the form of light enters into the case; an image capturing unit which is disposed in the case, and receives light incident through the opening of the case to obtain raw data; a control unit which performs data connection and alignment between three-dimensional data generated through image capturing of the image capturing unit, and determines whether an alignment error has occurred; and an actuator which vibrates when the alignment error has occurred.

12 Claims, 6 Drawing Sheets

(56) References Cited

U.S. PATENT DOCUMENTS

| | | | | |
|---|---|---|---|---|
| 6,319,006 | B1* | 11/2001 | Scherer | A61C 1/084 433/215 |
| 7,339,586 | B2* | 3/2008 | Guhring | G06T 7/30 345/426 |
| 9,730,776 | B2* | 8/2017 | Lal | A61C 9/0053 |
| 11,432,781 | B2* | 9/2022 | Turner | A61B 6/4233 |
| 12,042,351 | B2* | 7/2024 | Aamodt | A61C 13/0004 |
| 2005/0237324 | A1* | 10/2005 | Guhring | G06T 15/08 345/419 |
| 2006/0142657 | A1* | 6/2006 | Quaid | A61B 90/37 600/424 |
| 2006/0193521 | A1* | 8/2006 | England | G01S 17/42 382/190 |
| 2006/0275740 | A1* | 12/2006 | Singh | G06T 11/003 433/215 |
| 2006/0290695 | A1* | 12/2006 | Salomie | G06T 17/20 345/423 |
| 2008/0085489 | A1* | 4/2008 | Schmitt | A61C 1/084 433/75 |
| 2009/0079738 | A1* | 3/2009 | Liao | G06T 15/08 345/427 |
| 2009/0103793 | A1* | 4/2009 | Borland | G06T 15/08 382/131 |
| 2009/0316966 | A1* | 12/2009 | Marshall | G16H 50/30 382/128 |
| 2010/0124367 | A1* | 5/2010 | Cizek | G06T 7/33 382/132 |
| 2014/0142507 | A1* | 5/2014 | Armes | A61M 5/20 604/112 |
| 2017/0215698 | A1 | 8/2017 | Rynerson | |
| 2018/0068455 | A1 | 3/2018 | Lal et al. | |

FOREIGN PATENT DOCUMENTS

| | | |
|---|---|---|
| KR | 10-2017-0113412 A | 10/2017 |
| KR | 10-2018-0126166 A | 11/2018 |
| KR | 10-1977181 A | 5/2019 |
| KR | 10-2020-0016803 A | 2/2020 |
| WO | 2007-084727 A1 | 7/2007 |

OTHER PUBLICATIONS

Non-final office action mailed Apr. 18, 2022 from the Korean Patent Office for Korean Application No. 10-2021-0025633.

Final Office Action mailed Dec. 29, 2022 for Korean Application No. 10-2021-0025633.

* cited by examiner

ALIGNMENT STATE INDICATING APPARATUS AND METHOD

CROSS-REFERENCE TO RELATED APPLICATIONS

This application is a continuation application of International Application No. PCT/KR2021/002446, filed Feb. 26, 2021, which claims the benefit of Korean Patent Application Nos. 10-2020-0025433, filed Feb. 28, 2020; and 10-2021-0025633, filed Feb. 25, 2021, in the Korean Intellectual Property Office, the disclosures of which are incorporated herein in their entirety by reference.

TECHNICAL FIELD

The present disclosure relates to an alignment state indicating apparatus and a method using the same.

BACKGROUND ART

While three-dimensional (3D) printing technology that implements a file designed as digital data has already been spotlighted, a 3D scanning technology that converts a real existing object into digital data has also been continuously developed. The 3D scanning technology plays a key role in a CAD/CAM system, and in particular, is frequently used for prosthesis production and cure to meet a patient's oral structure by scanning the patient's oral cavity (which is used so as to include teeth, gums, and jawbones).

Meanwhile, while a user scans a patient's oral cavity by using a 3D oral scanner, it is required for the user to repeatedly check whether a 3D model is normally formed as viewing a screen of a display connected to the oral scanner. In this case, the user of the oral scanner mostly proceeds with the scanning in a manner that the user concentrates upon the patient's oral cavity, that is, a portion being scanned, and checks the display screen occasionally by turning the user's head. If the user continuously proceeds with the scanning in such a manner, user's fatigue increases rapidly, and thus user's concentration is degraded in the process of scanning the patient's oral cavity. This may cause reduction of data accuracy in obtaining the 3D model for the patient's oral cavity.

DISCLOSURE

Technical Problem

In order to solve the above problem, the present disclosure provides an alignment state indicating apparatus which enables a user to perceive an alignment error quickly and intuitively.

Further, the present disclosure provides an alignment state indicating method which enables a user who uses a scanner to intuitively perceive a state where connection and alignment are not normally performed (alignment error) between 3D data.

The technical problems of the present disclosure are not limited to the above-described technical problems, and other unmentioned technical problems may be clearly understood by those skilled in the art from the following descriptions.

Technical Solution

In order to solve the above object, the present disclosure provides an alignment state indicating apparatus, which includes: a case having an opening formed thereon and configured to be open so that an object in the form of light enters into the case; an imaging unit disposed in the case and configured to obtain raw data by receiving light incident through the opening of the case; a controller configured to perform data connection and alignment between 3D data generated through imaging of the imaging unit and to determine whether an alignment error occurs; and an actuator configured to vibrate in case that the alignment error occurs, and an alignment state indicating method implemented by the apparatus.

Specifically, in order to solve the drawback in that it is required to continuously check a display screen so as to perceive an existing alignment error, the present disclosure provides an alignment state indicating apparatus, in which if the alignment error occurs, an actuator vibrates to enable a user to intuitively perceive the alignment error, and an alignment state indicating method implemented by the apparatus.

Advantageous Effects

According to the present disclosure, data blank can be minimized by a user to additionally capture an image of an adjacent part of a part in which vibration is sensed by an actuator, and as a result, a precise 3D model can be obtained.

Further, since vibration is tactilely sensed in a situation where a user continuously keeps an eye on a patient's oral cavity to obtain scan data, a scanner user's quick response becomes possible.

MODE FOR INVENTION

Figure 1:
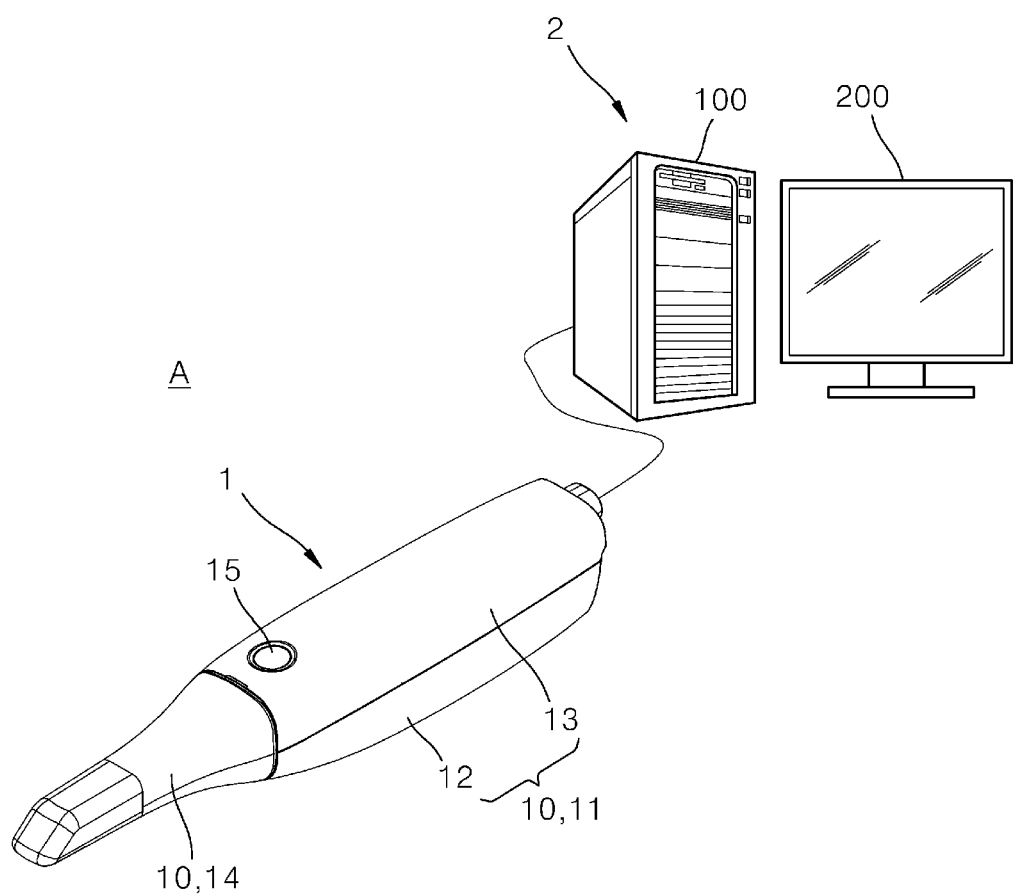
FIGS. 1 and 2 are diagrams explaining an alignment state indicating apparatus according to the present disclosure.

Hereinafter, some embodiments of the present disclosure will be described in detail with reference to the exemplary drawings. In adding reference numerals to constituent elements in the drawings, it is to be noted that the same constituent elements have the same reference numerals as much as possible even if they are represented in different drawings. Further, in explaining embodiments of the present disclosure, the detailed explanation of related known configurations or functions will be omitted if it is determined that the detailed explanation interferes with understanding of the embodiments of the present disclosure.

The terms, such as "first, second, A, B, (a), and (b)", may be used to describe constituent elements of embodiments of the present disclosure. The terms are only for the purpose of discriminating one constituent element from another constituent element, but the nature, the turn, or the order of the corresponding constituent elements is not limited by the terms. Further, unless otherwise defined, all terms (including technical and scientific terms) used herein have the same meanings as those commonly understood by those ordinary skilled in the art to which the present disclosure belongs. The terms that are defined in a generally used dictionary should be interpreted as meanings that match with the meanings of the terms from the context of the related technology, and they are not interpreted as an ideal or excessively formal meaning unless clearly defined in the present disclosure.

Figure 2:
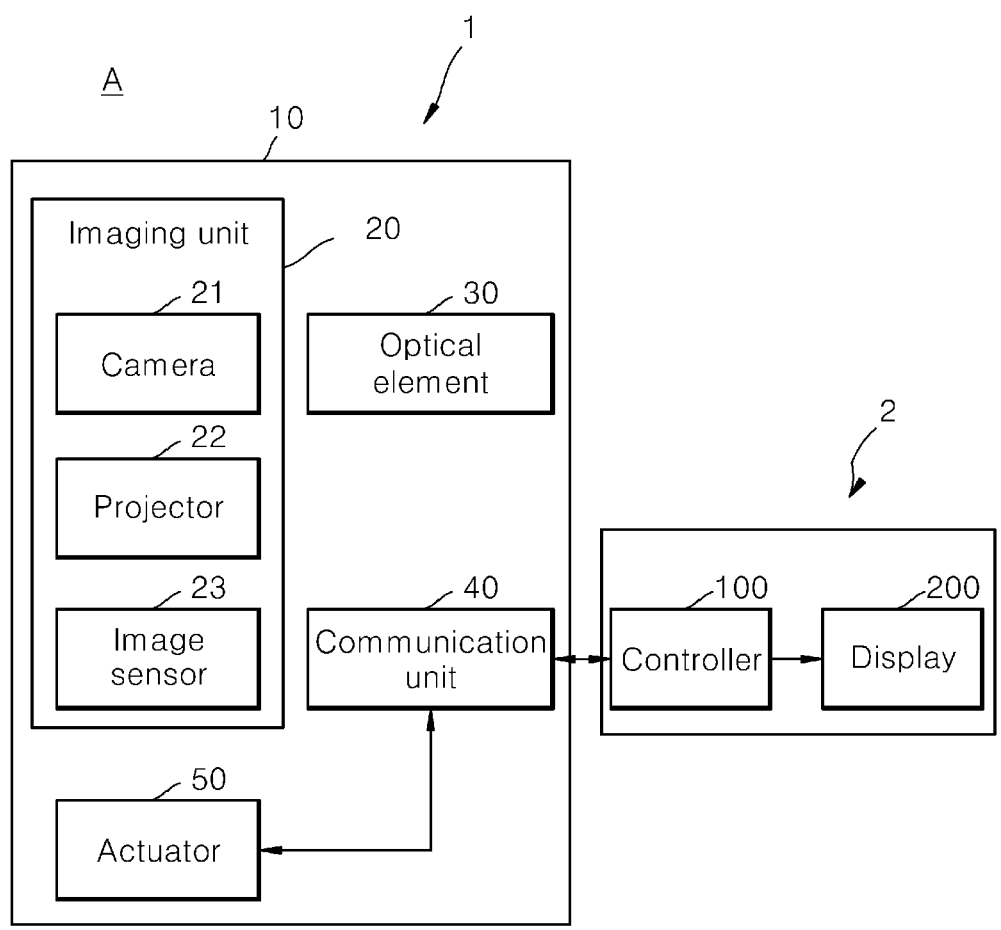

FIGS. 1 and 2 are diagrams explaining an alignment state indicating apparatus according to the present disclosure.

Referring to FIGS. 1 and 2, an alignment state indicating apparatus A according to the present disclosure may include: a case 10 capable of entering into and withdrawing from an oral cavity, and having an opening formed thereon, through which the shape of the oral cavity is incident into the case in the form of light through one end part thereof; and an imaging unit 20 disposed in an inside of the case 10 to receive light incident through the opening of the case 10, and obtaining raw data by a built-in imaging sensor 23.

The case 10 may be an exterior of a scanner 1 in the alignment state indicating apparatus A, which obtains image information, shape information, and color information on a patient's oral cavity through a scanning process, and generates data of the oral cavity based on the obtained information. The case 10 protects, from an external environment, constituent elements of the scanner 1 being disposed inside the case 10. The case 10 may include a body case 11 and a tip case 14. Exemplarily, the body case 11 may include a lower case 12 configuring a lower end of the body case 11, and an upper case 13 configuring an upper end of the body case 11. By a combination of the lower case 12 with the upper case 13, the constituent elements of the scanner 1 disposed inside the body case 11 can be protected from the external environment. Further, the tip case 14 has an opening formed on one side thereof to guide the incident light to the imaging unit 20, and protects the constituent elements disposed therein from the external environment in order to guide the light to the imaging unit 20. Meanwhile, the user may perform a scanning process by pressing a button 15 formed on the body case 11.

The scanner 1 may be formed in a handheld form. By using the handheld type scanner 1, the user may perform the scanning with free angles and distances with respect to an object, and may additionally scan the corresponding part with respect to a part having a poor scan quality.

Meanwhile, in the description, an actual oral cavity of a patient has been explained as an example of a scan object, but the scan object is not limited thereto. That is, in addition to the oral cavity, various scannable objects, that is, oral cavities to which dental prostheses, such as gypsum models, impression models, crowns, or implants, are applied may be used as the scan objects.

Hereinafter, detailed constituent elements disposed in the case 10 of the scanner 1 will be described.

The imaging unit 20 may include a camera 21 for obtaining received light from an opening formed at one end of the case 10, and the camera 21 constituting the imaging unit 20 may be a single camera or two or more multiple cameras. Exemplarily, like human eyes, the imaging unit 20 may include two or more cameras 21, and may obtain more precise data by imaging the same point at different angles and/or distances.

Meanwhile, the imaging unit 20 may include a projector 22 formed on one side of the camera 21 and configured to emit light through the opening. The projector 22 may generate light of a specific form, and the light generated in this case may be variously formed in accordance with a user's need. Exemplarily, the light generated by the projector 22 may have a wavelength in the visible light region. Further, the projector 22 may emit a structured light into the oral cavity in order to convert raw data obtained by the imaging unit 20 into 3D data having a specific volume. Exemplarily, the structured light may be of a stripe pattern in which highlights and shadows appear alternately, but is not limited thereto.

The light generated from the projector 22 and emitted toward the object (e.g., patient's oral cavity) is reflected from the surface of the object, and the light reflected from the surface of the object is incident through the opening of the scanner 1, and is received in the camera 21. The image sensor 23 formed on an imaging board obtains the raw data from the light received in the camera 21. Exemplarily, the image sensor 23 may be a CCD sensor or a CMOS sensor, but is not necessarily limited thereto, and the image sensor 23 may be any sensor for obtaining the raw data from the received light. In this case, the raw data may be 2D image or 3D image data obtained to generate a 3D model of the object. Exemplarily, the raw data may be data (e.g., 2D image data) obtained by the camera 21 included in the scanner when the object is scanned by using the scanner 1.

Further, at one end of the tip case 14, an optical element 30 for transferring the light incident into the scanner 1 to the imaging unit 20 may be formed. The optical element 30 may be formed of a material that can refract and reflect the light, and exemplarily, the optical element 30 may be a mirror or a prism. The light being transferred to the imaging unit 20 by the optical element 30 may be the light reflected from the object, and the light may be obtained as the light emitted from the projector 22 is reflected from the surface of the object. The process in which the light received in the camera 21 through the optical element 30 is converted into the raw data by the image sensor 23 is as described above.

Meanwhile, the raw data obtained by the operation of the imaging unit 20 may be transmitted to a data processing device 2 that is formed spaced apart from the scanner 1 to be converted into 3D data. In this case, the 3D data may be generated based on a plurality of the raw data. Further, the 3D data may be generated based on the plurality of the raw data, and may be a 3D model generated through performing of data connection and alignment between the 3D data. The alignment process may be performed in various methods, and exemplarily, it may be performed by using an iterative closest point (ICP) method.

Meanwhile, the scanner 1 further includes a communication unit 40. The communication unit 40 may transmit the raw data obtained by the scanner 1 to the data processing device 2. In case that the scanner 1 and the data processing device 2 are connected by wire, the communication unit 40 transmits the raw data stored in the scanner 1 to the data processing device 2 through the wire. In case that the scanner 1 and the data processing device 2 are wirelessly connected, the communication unit 40 transmits the raw data stored in the scanner 1 to the data processing device 2 by using a communication method, such as Wi-Fi or ZigBee.

Although not illustrated in the drawing, the scanner 1 may further include a storage unit. If the raw data is obtained from the imaging unit 20, the obtained raw data may be temporarily stored in the storage unit. The raw data stored in the storage unit may be transmitted through the communication unit 40 when the scanner 1 and the data processing device 2 are connected to each other.

The data processing device 2 may be connected to a wired or wireless communication network through the communication unit 40 of the scanner 1. The data processing device 2 may be a computing device, such as a laptop computer, a smart phone, a desktop computer, a PDA, or a tablet PC, but is not limited thereto.

Further, the data processing device 2 may include a controller 100 and a display 200. More specifically, the controller 100 may determine an alignment error by performing connection and alignment between the 3D data, and may control the actuator 50 to vibrate. The display 200 may visually display a user interface (UI) to show the converted 3D data representing the patient's oral cavity. Further, if an error occurs in the alignment performing process, the display 200 may visually display an error occurrence part.

Meanwhile, although the controller 100 is indicated as a separate configuration from the scanner 1 in FIGS. 1 and 2, the controller 100 is not limited thereto, and may be included in the scanner1. Exemplarily, if the data processing device 2 transfers an error occurrence signal to the scanner 1 after determining the alignment error, the controller (not illustrated) formed in the scanner may control the actuator 50 to vibrate.

Further, the alignment state indicating apparatus A according to the present disclosure may include the actuator 50. In this case, the actuator 50 may be configured to generate vibration through its rotation operation. The actuator 50 may perform data connection and alignment between 3D data generated through imaging of the imaging unit 20, and if an error occurs in the alignment performing process, the actuator 50 may operate to vibrate. In the description, the alignment error may mean a state where the connection and alignment between the 3D data is not continuous. The alignment error may occur in case that there is not an overlapping part when the 3D data are connected to each other, or the overlapping part formed between the 3D data has low data reliability.

Hereinafter, the operation of the actuator 50 will be described in detail together with the operation of the data processing device 2. The controller 100 of the data processing device 2 may convert the raw data transmitted from the scanner 1 into the 3D data, and may perform the alignment process by using the overlapping part between the 3D data. If there is not a common point between the 3D data, or the common point has low reliability during performing the alignment process, the corresponding part is determined as the alignment error. In order to notify the user of the point that is determined as the alignment error, the controller 100 may apply a control signal to the actuator 50 through the communication unit 40 of the scanner 1. The actuator 50 may vibrate intermittently or continuously based on the control signal applied from the controller 100. Exemplarily, if the controller of the data processing device 2 determines that the data connection and alignment between the 3D data is not normally performed, the actuator 50 may operate to vibrate once for a predetermined time. Further, if the controller of the data processing device 2 determines that the data connection and alignment between the 3D data is not normally performed, the actuator 50 may stop its operation after vibrating once.

The actuator 50 may be in any form that is formed to be built in the case 10, and if the scanner 1 is in the handheld form, the actuator 50 may be formed to be adjacent to the part gripped by the user who scans the patient's oral cavity, that is, to the inside of the body case 11. Disposing of the actuator inside the body case 11 may not cause inconvenience to the patient in such a manner that unintended impact can be prevented from being applied to the patient's oral cavity due to the vibration while the part of the tip case 14 enters into the oral cavity and the scanning is performed.

Figure 3:
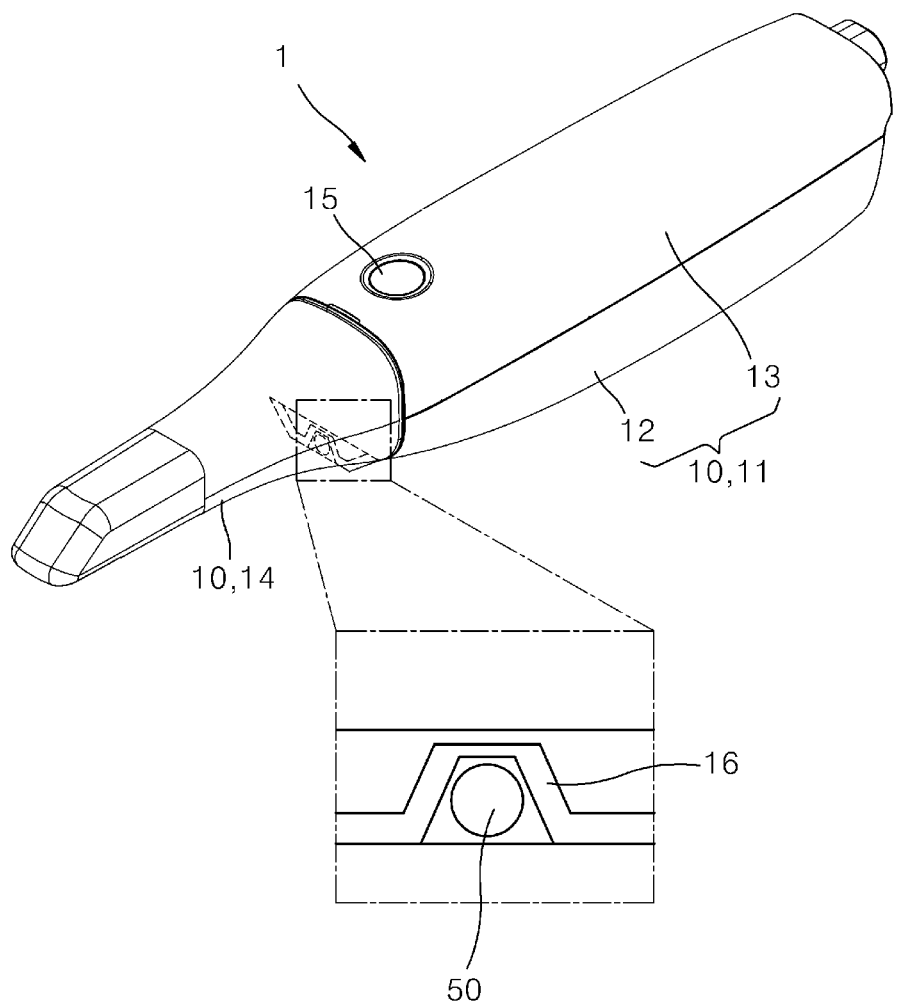
FIG. 3 is a diagram explaining a location where an actuator is formed in an alignment state indicating apparatus according to the present disclosure.

More specifically, referring to FIG. 3, the actuator 50 may be disposed at one end of an inside of the lower case 12 that forms a lower end of the case 10. Exemplarily, the actuator 50 may be disposed at one end that is adjacent to the tip case 14 among ends of the inside of the lower case 12. The user can grip the outer surface of the lower case 12 at a location where the actuator 50 is disposed. The actuator 50 is formed adjacent to the location where the user grips the scanner 1, and thus has an advantage that the user can promptly perceive the error when the alignment error occurs. That is, since the user typically surrounds one end of the upper case 13 with the user's thumb, and surrounds one end of the lower case 12 with the remaining fingers (index finger, middle finger, ring finger, and little finger), the user can easily perceive the vibration of the actuator 50 disposed at one end of the lower case 12. Further, since the actuator 50 is disposed at one end that is adjacent to the tip case 14 among the ends of the inside of the lower case 12, it is possible to minimize the unintended impact being applied to the patient's oral cavity caused by the vibration being generated by the actuator 50 as compared with the vibration being generated by the actuator 50 formed at the other end of the inside of the lower case 12.

Further, at least a part of an outer periphery of the actuator 50 is covered by a frame 16 formed on the inside of the lower case 12. The frame 16 may be formed in a bent shape to cover the part of the outer periphery of the actuator 50, but the shape of the frame 16 is not limited thereto. Since the frame 16 covers the part of the outer periphery of the actuator 50, the vibration generated by the actuator 50 is attenuated by the frame 16, and the strength of the vibration on the lower case 12 that is gripped by the user is decreased, thereby minimizing the unintended impact being applied to the patient's oral cavity during the scanning. Further, since the frame 16 serves as a vibration damper, it can minimize the influence on the imaging unit 20 due to the vibration, and can obtain clear raw data and 3D data. Meanwhile, the frame 16 may be formed of a metal material in order to effectively attenuate the vibration of the actuator 50.

Figure 4:
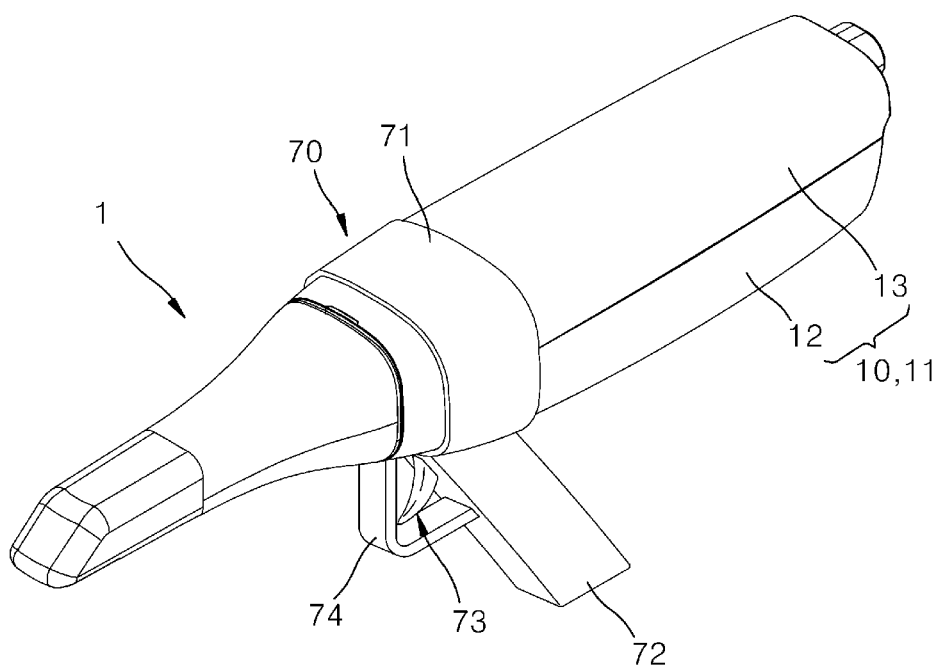
FIG. 4 is a diagram explaining a scanner to which a handle is applied in an alignment state indicating apparatus according to the present disclosure.

FIG. 4 is a diagram explaining a scanner to which a handle 70 is applied in an alignment state indicating apparatus according to the present disclosure.

Referring to FIG. 4, the scanner 1 constituting the alignment state indicating apparatus A may be formed in a gun shape, which further includes a handle 70 combined and integrally formed with the outer surface of the case 10. In this case, the handle 70 may include a trigger 73 being pressed by at least one finger of the user and operating to turn on/off the scanning process. The trigger 73 is formed in a trigger shape, and if the trigger is pressed, the scanning process is performed, whereas if the pressing is stopped, the scanning process is also stopped. For example, if the user presses the outer surface of the trigger with the user's index finger, the scanning may be performed, whereas if the pressing is not performed (if the pressing is stopped), the scanning may be stopped.

Meanwhile, the handle 70 may include a cover part 71 that covers the part of the outer surface of the case 10, and a gripping part 72 formed to extend in one direction from the outer surface of the case 10 and formed so that an outer surface thereof is surrounded by other fingers of the user except the finger that presses the trigger 73. The outer surface of the gripping part 72 may be gripped around by other fingers that are not located on the trigger 73. For example, in case that the user operates the trigger 73 by using the index finger, the remaining fingers (index finger, middle finger, ring finger, and little finger) of the user may grip the outer surface of the gripping part 72. As described above, since the handle 70 including the trigger 73 and the gripping part 72 is additionally formed, the user can perform the scanning by pressing the trigger 73 while gripping the handle 70. The trigger 73 may perform the same role as that of the button 15 as described above. Since the handle 70 is formed, the user can easily aim at the object without directly gripping the body of the case of the scanner 1, and thus precise scanning becomes possible.

Further, the handle 70 may additionally include a trigger protector 74 spaced apart from the outer surface of the trigger 73, and formed between the cover part 71 and the gripping part 72. Through an inner space formed between the trigger protector 74 and the trigger 73, at least one finger (e.g., index finger) of the user for pressing the trigger 73 as described above can be inserted and accommodated, and in this case, the trigger 73 is determined to perform scanning or to stop scanning only depending on whether the trigger 73 is pressed by the index finger of the user. Since the trigger protector 74 is formed, unnecessary scanning can be prevented from being performed through pressing of the trigger 73 by another unintended object. Meanwhile, the trigger protector 74 is formed to have a ring-shaped space in a vertical direction to a length direction of the case 10, and the user's finger can be easily accommodated therein.

In case that the scanner 1 includes the gun-shaped handle 70 as described above, the actuator 50 may be formed so as to be built in the gripping part 72 of the handle 70. In this case, the user can easily sense the vibration of the actuator 50 built in the gripping part 72 with other fingers of the user except the finger located on one surface of the trigger 73, and thus the user can efficiently sense the alignment state (whether the alignment error occurs).

Hereinafter, an alignment state indicating method according to the present disclosure will be described in detail.

Figure 5:
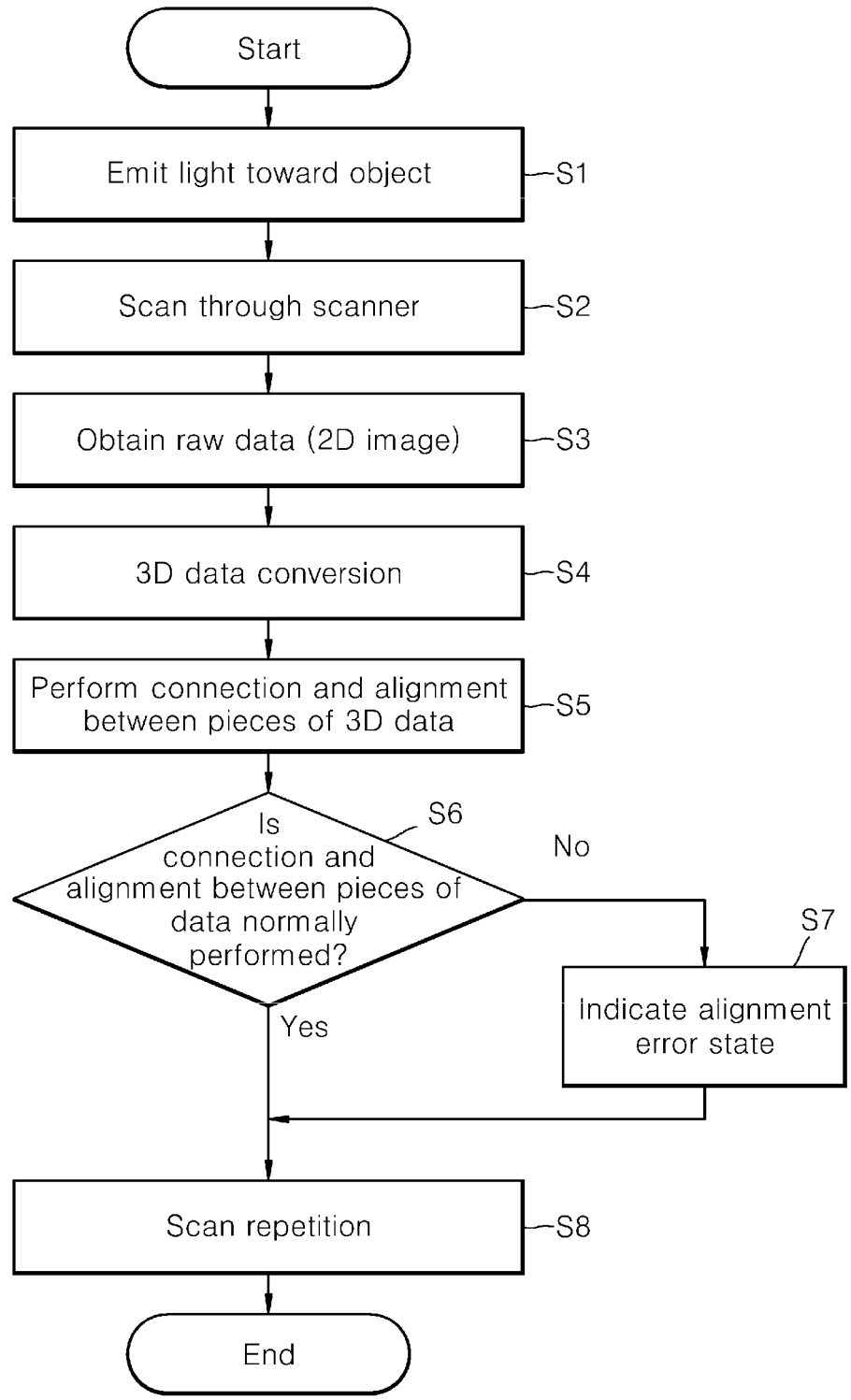
FIG. 5 is a flowchart of an alignment state indicating method according to the present disclosure.
Figure 6:
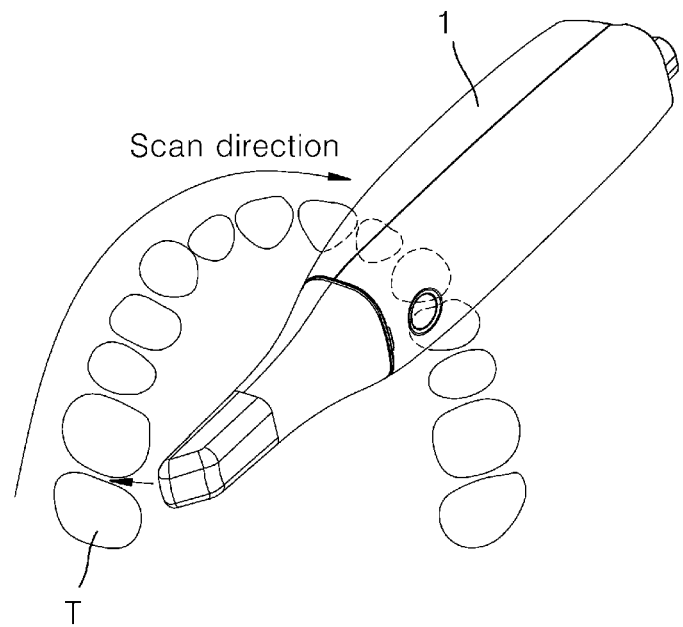
FIG. 6 is a conceptual diagram explaining scanning through a scanner in an alignment state indicating method according to the present disclosure.
Figure 7:
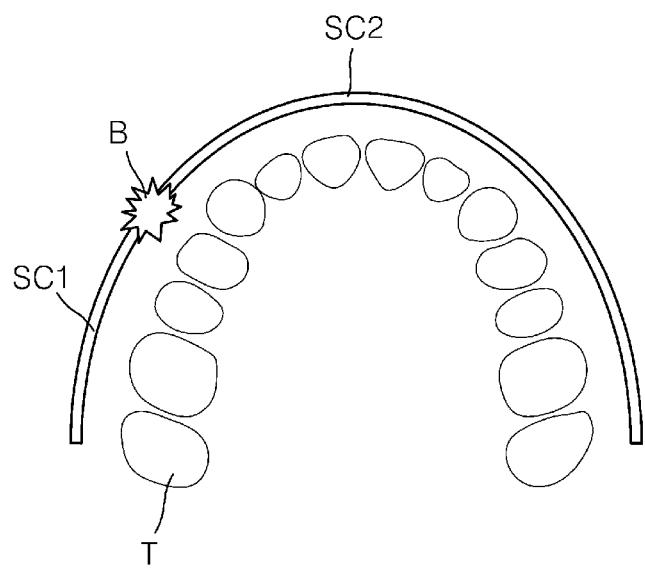
FIG. 7 is a conceptual diagram indicating a state where alignment is broken and data blank occurs in an alignment state indicating method according to the present disclosure.

FIG. 5 is a flowchart of an alignment state indicating method according to the present disclosure, FIG. 6 is a conceptual diagram explaining scanning through a scanner in an alignment state indicating method according to the present disclosure, and FIG. 7 is a conceptual diagram indicating a state where alignment is broken and data blank occurs in an alignment state indicating method according to the present disclosure.

Referring to FIG. 5, an alignment state indicating method according to the present disclosure may include: a scanning step (S2) of scanning an oral cavity that is an object through a scanner; a raw data obtaining step (S3) in which an imaging part formed inside the scanner forms raw data through light incident into the scanner in the scanning step (S2); a 3D data conversion step (S4) of generating 3D data from the raw data; an alignment step (S5) of performing data connection and alignment between the 3D data generated in the 3D data conversion step; an alignment checking step (S6) of determining whether the connection and alignment between the 3D data is normally performed; and a feedback step (S7) of indicating an alignment error state by an operation of an actuator built in the scanner if it is determined that the connection and alignment between the 3D data is not normally performed in the alignment checking step. Hereinafter, the respective steps will be described in detail.

The scanning step (S2) may be a step of scanning the oral cavity that is the object T through the scanner. Referring to FIG. 6, a scanner user (typically, a dentist who diagnoses and treats patients may be the user) may grip the handheld type scanner with the user's hand, and may scan the patient's oral cavity that is the object T to be scanned. On the whole, the user may continuously scan teeth formed in the patient's oral cavity from one direction to the other direction, and as needed, the user may additionally scan a part on which the scanning has been insufficiently performed. When performing the scanning step (S2), as needed, the scanner may emit a specific light toward the object (light emitting step (S1)). The light emitted toward the object may be generated by a projector built in the scanner, and the kind of the generated light is as described above.

Further, the raw data obtaining step (S3) may be a step in which the imaging unit forms the raw data (e.g., 2D image) through the light incident into the scanner in the above-described scanning step (S2). Meanwhile, the imaging unit may include at least one camera formed inside the body case as described above. In the specification, "at least one camera" may be one single camera, or multiple cameras composed of two or more cameras. Further, the imaging unit may include an imaging sensor connected in telecommunication with the camera. The imaging sensor may serve to generate the raw data by analyzing the light incident through the camera.

Further, the 3D data conversion step (S4) may be a step of converting the raw data obtained in the above-described raw data obtaining step (S3) into the 3D data. Specifically, in order to convert the 2D image of the imaged oral cavity into the 3D data having a volume, the brightness value of each pixel of the 2D image may be used. Further, in order to collect information required to convert the 2D image into the 3D data, light in the form of a structured light may be emitted onto the object in the light emitting step (S1).

Further, the alignment step (S5) may be a step of overlapping and aligning the obtained 3D data so that overlapping parts of the 3D data are connected with each other. Through the continuous imaging and data obtaining as described above, the upper jaw, lower jaw, and occlusion data of the patient can be obtained, and as a result, one 3D model is completed as the upper jaw, lower jaw, and occlusion data are connected and aligned with one another.

Further, the alignment checking step (S6) may be a step of identifying whether the overlapping parts of the 3D data exist, and whether the data are connected and aligned with one another.

Further, the feedback step (S7) may be a step in which the scanner 1 indicates an error state if it is determined that the data connection and alignment between the 3D data is not normally performed in the alignment checking step (S6). In this case, the feedback in the present disclosure may mean a step of performing a notification so that the user of the scanner 1 can perceive the alignment error state, and as an example, the user can perceive the alignment error state by the vibration of the actuator.

Hereinafter, a process of performing the feedback step (S7) will be described in detail. Specifically, if it is determined that the connection and alignment between the 3D data is not normally performed, the actuator may operate to vibrate continuously in the feedback step (S7). That is, if the alignment error occurs, the actuator may operate to continuously vibrate, and if the vibration occurs in the scanner, the user may perceive that the alignment error has occurred. Accordingly, when performing the scanning step (S2), the user may perform an additional scanning with respect to the vibration occurrence part. If it is determined that the connection and alignment between the 3D data is normally performed again through the additional scanning, the actuator may stop the vibration, and as a result, the user can obtain the 3D oral model having high reliability by stably performing scanning of the patient's oral cavity.

Further, the actuator may operate to vibrate once for a predetermined time. In this case, the time when the actuator vibrates may be set to a length on which the vibration exerts a minimum influence when the user performs the scanning. Further, the time when the actuator vibrates may be set to a length that does not cause inconvenience to the patient in such a manner that an impact is not applied to the teeth due to the vibration of the actuator. The time when the actuator vibrates to notify the alignment error in the feedback step (S7) may be momentarily about 1 second or less. Exemplarily, when the alignment error occurs in the feedback step (S7), the actuator may operate to vibrate once for an initial 0.2 second. Selectively, if it is determined that the data connection and alignment between the 3D data is normally performed after the actuator vibrates once for the predetermined time, the actuator may stop the vibration. Accordingly, if the user feels the vibration on the scanner, the user can easily perceive the alignment error occurrence.

According to another embodiment, even in the scanning step (S2), it can be indicated that the scanning is normally performed and the data connection and alignment between the 3D data is performed through the operation of the actuator. Exemplarily, in the scanning step (S2), the actuator may operate to vibrate intermittently at predetermined intervals. Any intervals to the extent that the user can perceive can be freely set. For example, in the scanning step (S2), the actuator may intermittently vibrate so as to have a vibration time of about 0.1 to 0.5 second and a rest time of about 2 to 5 seconds, and the user may easily perceive the state where the scanning is normally performed.

If the normal scanning and alignment is performed by the above-described vibration characteristics, the actuator may intermittently vibrate at the predetermined intervals, whereas if a problem occurs in the scanning and alignment, the actuator may vibrate continuously or intermittently, so that the user can easily perceive whether the oral cavity is normally scanned.

Meanwhile, if a problem occurs in the scanning process and the alignment process, the actuator may vibrate stronger and/or longer than as compared with the case where the normal scanning and alignment is performed, and thus the user can perceive the alignment error more accurately. As described above, the feedback of the alignment error occurrence through the vibration of the actuator may be selectively applied in accordance with a user's need, and whether to turn on/off the function for the actuator vibration when the alignment error occurs may be set on a user interface of an application (program) for performing the scanning process.

Referring to FIGS. 6 and 7, the user may grip the handheld type oral scanner with the user's hand, and may scan the patient's oral cavity that is the object T to be scanned. The scanner 1 may continuously receive an image of the patient's oral cavity, and the input image may be converted into the 3D data by the data processing device. Meanwhile, if the object is unable to be sufficiently scanned in the process of scanning the object T, a part in which connection between data becomes unclear may occur, and the part remains as a data blank B.

As described above, if the data blank B occurs, the data scanned after the data blank B occurs is unable to be connected and aligned with the scan data before the data blank B occurs. Exemplarily, if the user is unable to proceed with a careful scan at the middle point of the scan path while the scanner 1 performs the scanning in accordance with the scan direction, the data blank B occurs. That is, although the connection and alignment between the 3D data may have been normally performed up to a first scan area SC1, the second scan area SC2 being scanned after the data blank B occurs does not have a clear data connection relationship with the first scan area SC1, and thus it is difficult to proceed with any further additional scan. If the alignment error occurs as described above, the vibration of the actuator is generated, and thus the user can promptly and intuitively perceive the vibration of the actuator through the touch of the hand that grips the scanner 1. Meanwhile, when the alignment error is notified through the vibration of the actuator, various vibration intensities and vibration periods (which may include continuous or intermittent vibrations) may be used.

If the alignment error is dissolved by the alignment checking step (S6) and the feedback step (S7), the scanning is repeated (repetition step (S8)). The scan repetition may mean that the scanning step (S2) is continuously performed, and the user can obtain the precise 3D model data by collecting a sufficient amount of data for the object.

The above explanation of the present disclosure is merely for exemplary explanation of the technical idea of the present disclosure, and various changes and modifications may be possible in a range that does not deviate from the essential characteristics of the present disclosure by those of ordinary skill in the art to which the present disclosure pertains.

Accordingly, embodiments disclosed in the present disclosure are not to limit the technical idea of the present disclosure, but to explain the technical idea, and the scope of the technical idea of the present disclosure is not limited by such embodiments. The scope of the present disclosure should be interpreted by the appended claims, and all technical ideas in the equivalent range should be interpreted as being included in the scope of the present disclosure.

EXPLANATION OF SYMBOLS

A: alignment state indicating apparatus
1: scanner 10: case
11: body case 12: lower case
13: upper case 14: tip case
15: button 16: frame
20: imaging unit 21: camera
22: processor 23: image sensor
30: optical element 40: communication unit
50: actuator 70: handle
71: cover part 72: gripping part
73: trigger 74: trigger protector
2: data processing device 100: controller
200: display
S1: light emitting step S2: scanning step
S3: raw data obtaining step S4: 3D data conversion step
S5: alignment step S6: alignment checking step
S7: feedback step S8: repetition step
T: object SC1: first scan area
SC2: second scan area B: data blank

INDUSTRIAL APPLICABILITY

The present disclosure is to provide an alignment state indicating apparatus and an alignment state indicating method, in which a user who uses a scanner can intuitively perceive a state where connection and alignment between 3D data is not normally performed (alignment error).

The invention claimed is:

1. An alignment state indicating apparatus comprising:
a case having an opening formed thereon and configured to be open so that an object in the form of light enters into the case;
an imaging unit disposed in the case and configured to obtain raw data by receiving light incident through the opening of the case;
a controller configured to perform data connection and alignment between 3D data generated through imaging of the imaging unit and to determine whether an alignment error occurs; and
an actuator configured to vibrate in case that the alignment error occurs,
wherein at least a part of an outer periphery of the actuator is covered by a frame formed on the inside of the case, and
wherein vibration generated by the actuator is attenuated by the frame.

2. The alignment state indicating apparatus of claim 1, wherein the actuator is formed inside the case, wherein the case is adapted to be gripped by a user.

3. The alignment state indicating apparatus of claim 2, wherein the actuator is disposed at one end of an inside of a lower case that forms a lower end of the case.

4. The alignment state indicating apparatus of claim 1, further comprising a handle combined and formed integrally with an outer surface of the case,
wherein the handle includes a trigger configured to turn on/off a scanning process by being pressed by at least one finger of a user, and a gripping part formed to extend in one direction from the outer surface of the case and formed so that an outer surface thereof is surrounded by other fingers of the user except the finger that presses the trigger.

5. The alignment state indicating apparatus of claim 4, wherein the actuator is formed on an inside of the gripping part.

6. The alignment state indicating apparatus of claim 1, further comprising a display configured to visually display an error occurrence part when the error occurs in an alignment performing process.

7. An alignment state indicating method comprising:
a scanning step of scanning an object through a scanner;
a raw data obtaining step of obtaining raw data by receiving light incident to an inside of the scanner;
a 3D data conversion step of generating 3D data from the raw data;
an alignment step of performing data connection and alignment between the 3D data generated in the 3D data conversion step;
an alignment checking step of determining whether the connection and alignment between the 3D data is normally performed; and
a feedback step of indicating an alignment error state by an operation of an actuator built in the scanner if it is determined that the connection and alignment between the 3D data is not normally performed in the alignment checking step,
wherein the scanner includes a case and at least a part of an outer periphery of the actuator is covered by a frame formed on the inside of the case, and
wherein vibration generated by the actuator is attenuated by the frame.

8. The alignment state indicating method of claim 7, wherein the actuator performing the feedback step is formed adjacent to a part that is gripped by a user who performs scanning.

9. The alignment state indicating method of claim 8, wherein the actuator is disposed at one end of an inside of a lower case that forms a lower end of the case.

10. The alignment state indicating method of claim 7, wherein if it is determined that the connection and alignment between the 3D data is not normally performed in the alignment checking step, the actuator operates to vibrate once for a predetermined time in the feedback step.

11. The alignment state indicating method of claim 10, wherein if it is determined that the connection and alignment between the 3D data is normally performed after the actuator vibrates once for the predetermined time, the actuator stops vibrating.

12. The alignment state indicating method of claim 7, wherein if it is determined that the connection and alignment between the 3D data is not normally performed in the alignment checking step, the actuator stops its operation after the actuator vibrates once in the feedback step.

* * * * *